(12) United States Patent
Kawamura

(10) Patent No.: US 11,969,281 B2
(45) Date of Patent: Apr. 30, 2024

(54) IMAGE PROCESSING APPARATUS, METHOD, AND PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 210 days.

(21) Appl. No.: 17/063,767

(22) Filed: Oct. 6, 2020

(65) Prior Publication Data

US 2021/0106298 A1    Apr. 15, 2021

(30) Foreign Application Priority Data

Oct. 9, 2019   (JP) .................................. 2019-185961

(51) Int. Cl.
*A61B 6/00* (2006.01)
*A61B 6/42* (2024.01)
*A61B 6/50* (2024.01)
*G06T 5/20* (2006.01)
*G06T 5/50* (2006.01)

(52) U.S. Cl.
CPC .............. *A61B 6/50* (2013.01); *A61B 6/4266* (2013.01); *A61B 6/481* (2013.01); *A61B 6/5241* (2013.01); *A61B 6/5282* (2013.01); *G06T 5/20* (2013.01); *G06T 5/50* (2013.01); *G06T 2207/10116* (2013.01); *G06T 2207/20224* (2013.01); *G06T 2207/30008* (2013.01)

(58) Field of Classification Search
CPC ......... A61B 6/50; A61B 6/4266; A61B 6/481; A61B 6/5241; A61B 6/5282; A61B 6/482; G06T 5/20; G06T 5/50; G06T 2207/10116; G06T 2207/20224; G06T 2207/30008
See application file for complete search history.

(56) References Cited

U.S. PATENT DOCUMENTS

| | | | | |
|---|---|---|---|---|
| 6,075,877 A | * | 6/2000 | Takeo | G06T 5/004 378/98.12 |
| 2003/0147497 A1 | * | 8/2003 | Avinash | G06T 5/20 378/98.9 |
| 2006/0029183 A1 | * | 2/2006 | Borghese | G06T 5/008 378/62 |
| 2007/0104317 A1 | * | 5/2007 | Ohishi | A61B 6/504 378/98.12 |

(Continued)

FOREIGN PATENT DOCUMENTS

| | | |
|---|---|---|
| JP | 2011-255060 A | 12/2011 |
| JP | 2014-207958 A | 11/2014 |

(Continued)

OTHER PUBLICATIONS

J. M. Boon and J. A. Seibert: Analytical model of the scattered radiation distribution in diagnostic radiology, Med. Phys. 15(5), Sep./Oct. 1988; p. 721-p. 725.

(Continued)

*Primary Examiner* — Mekonen T Bekele

(74) *Attorney, Agent, or Firm* — Studebaker & Brackett PC

(57) ABSTRACT

An image generation unit generates a contrast-reduced image in which contrast in a region other than a soft part is reduced in a radiographic image indicating a subject including the soft part and a bone part. A body thickness derivation unit derives the body thickness of the subject based on the contrast-reduced image.

20 Claims, 4 Drawing Sheets

(56) References Cited

U.S. PATENT DOCUMENTS

| | | | |
|---|---|---|---|
| 2011/0305405 A1 | 12/2011 | Kawamura | |
| 2015/0379711 A1 | 12/2015 | Imai | |
| 2016/0140720 A1 | 5/2016 | Naito | |
| 2018/0240224 A1* | 8/2018 | Fukuda | ................... G06T 5/50 |

FOREIGN PATENT DOCUMENTS

| | | | | |
|---|---|---|---|---|
| JP | 2015-043959 A | | 3/2015 | |
| JP | 2018-117900 A | | 8/2018 | |
| JP | 2018-153605 A | | 10/2018 | |
| JP | 2018153605 A | * | 10/2018 | ........... A61B 5/4872 |

OTHER PUBLICATIONS

An Office Action; "Decision of Refusal," mailed by the Japanese Patent Office dated Jan. 17, 2023, which corresponds to Japanese Patent Application No. 2019-185961 and is related to U.S. Appl. No. 17/063,767; with English language translation.

An Office Action; "Notice of Reasons for Refusal," mailed by the Japanese Patent Office dated Nov. 8, 2022, which corresponds to Japanese Patent Application No. 2019-185961 and is related to U.S. Appl. No. 17/063,767; with English language translation.

* cited by examiner

IMAGE PROCESSING APPARATUS, METHOD, AND PROGRAM

CROSS-REFERENCE TO RELATED APPLICATIONS

This application claims priority from Japanese Patent Application No. 2019-185961, filed Oct. 9, 2019 the disclosure of which is incorporated herein by reference in their entirety.

BACKGROUND

Technical Field

The present disclosure relates to image processing apparatus, method, and program for deriving a body thickness of a subject included in a radiographic image.

Related Art

In the related art, in the case of imaging radiographic images of a subject with radiations transmitted through the subject, in a case where a thickness of the subject is especially large, the radiations are scattered in the subject, and scattered radiations are generated. Thus, there is a problem that contrast of the acquired radiographic images is reduced due to the scattered radiations. Thus, in the case of imaging the radiographic images, imaging may be performed by providing a scattered radiation removal grid (hereinafter, simply referred to as a grid) between the subject and radiation detectors such that the radiation detectors that acquire the radiographic images by detecting the radiations are not irradiated with the scattered radiations. In the case of performing the imaging using the grid, since the radiation detectors are difficult to be irradiated with the radiations scattered by the subject, the contrast of the radiographic images can be improved.

The radiographic images are captured without using the grid, and an image quality improvement effect obtained by removing the scattered radiations using the grid is given to the radiographic images by image processing (see JP2014-207958A). The method described in JP2014-207958A is a method of performing scattered radiation removal processing by acquiring characteristics of the grid assumed to be used for removing the scattered radiations in the case of imaging the radiographic images, estimating scattered radiation components included in the radiographic images based on the grid characteristics and a body thickness distribution of the subject, and using the estimated scattered radiation components. A method of performing the scattered radiation removal processing by estimating the body thickness distribution of the subject and estimating the scattered radiation components by using the estimated body thickness distribution has been proposed (see JP2015-043959A).

Incidentally, in the methods described in JP2014-207958A and JP2015-043959A, it is important to accurately estimate the scattered radiation components. In order to accurately estimate the scattered radiation components, it is important to accurately estimate the body thickness distribution of the subject. However, the subject includes not only soft parts such as muscle and fat but also bone parts. In the radiographic images, since the bone part has contrast higher than the soft part, in a case where the body thickness distribution is derived based on the radiographic images, the body thickness is derived such that a body thickness of a part at which the bone part is present is greater than the original body thickness due to the influence of the bone part.

SUMMARY

The present disclosure has been made in view of the above circumstances, and an object of the present disclosure is to accurately derive a body thickness of a subject.

An image processing apparatus according to the present disclosure comprises an image generation unit that generates a contrast-reduced image in which contrast in a region other than a soft part is reduced in a radiographic image indicating a subject including the soft part and a bone part, and a body thickness derivation unit that derives a body thickness of the subject based on the contrast-reduced image.

"Reducing the contrast in the region other than the soft part" means mainly reducing the contrast in the region of the bone part. By performing the process of reducing the contrast of the region other than the soft part, the processing of reducing the contrast may be performed on a part of the region of the soft part adjacent to the region other than the soft part. "Reducing the contrast of the region other than the soft part" according to the present disclosure also includes that the contrast of a part of the region of the soft part adjacent to the region other than the soft part is reduced.

An image processing method according to the present disclosure comprises generating a contrast-reduced image in which contrast in a region other than a soft part is reduced in a radiographic image indicating a subject including the soft part and a bone part, and deriving a body thickness of the subject based on the contrast-reduced image.

An image processing program causing a computer to execute the image processing method according to the present disclosure may be provided.

Another image processing apparatus according to the present disclosure comprises a memory that stores a command to be executed by a computer, and a processor configured to execute the stored command. The processor executes processing of generating a contrast-reduced image in which contrast in a region other than a soft part is reduced in a radiographic image indicating a subject including the soft part and a bone part and deriving a body thickness of the subject based on the contrast-reduced image.

According to the present disclosure, a body thickness of a subject can be accurately derived.

DETAILED DESCRIPTION

Figure 1:
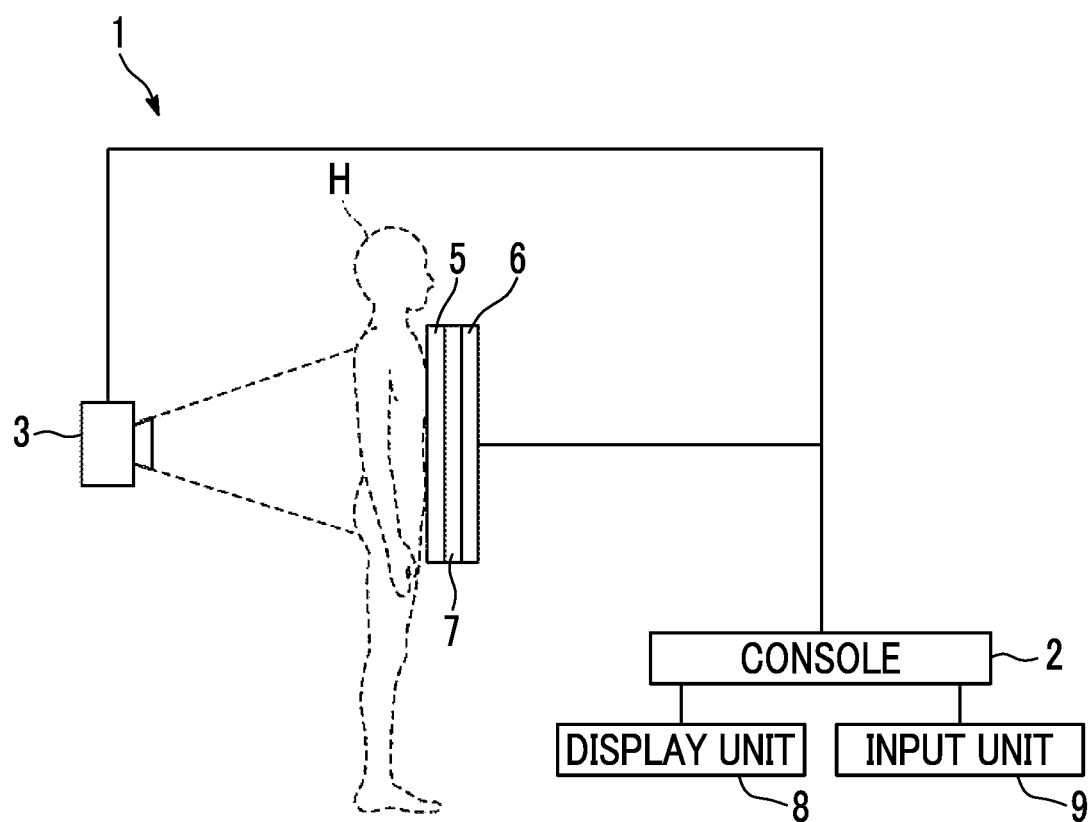
FIG. 1 is a schematic configuration diagram of a radiographic image imaging apparatus to which an image processing apparatus according to a first embodiment of the present disclosure is applied.

Hereinafter, embodiments of the present disclosure will be described with reference to the drawings. FIG. 1 is a schematic block diagram showing a configuration of a radiographic image imaging system to which an image processing apparatus according to a first embodiment of the present disclosure is applied. As shown in FIG. 1, the radiographic image imaging system according to the present embodiment can image two radiographic images having different energy distributions and can perform energy subtraction processing by using the two radiographic images, and includes an imaging apparatus 1 and a console 2 incorporating the image processing apparatus according to the present embodiment.

The imaging apparatus 1 is an imaging apparatus capable of performing energy subtraction using a so-called one-shot method of irradiating a first radiation detector 5 and a second radiation detector 6 with radiations such as X-rays which is emitted from a radiation source 3 and is transmitted through a subject H while changing energies. In the case of performing the imaging, the first radiation detector 5, a radiation energy conversion filter 7 made of a copper plate, and the second radiation detector 6 are arranged in this order from a side closer to the radiation source 3 as shown in FIG. 1, and the radiation source 3 is driven. The first and second radiation detectors 5 and 6 and the radiation energy conversion filter 7 are closely attached to each other.

Accordingly, the first radiation detector 5 acquires a first radiographic image G1 of the subject H by a low energy radiation including so-called soft rays. The second radiation detector 6 acquires a second radiographic image G2 of the subject H by a high energy radiation from which the soft rays are removed. The first and second radiographic images are input to the console 2. In the present embodiment, in the case of imaging the subject H, a scattered radiation removal grid that removes scattered radiation components of the radiations transmitted through the subject H is not used. Thus, the first radiographic image G1 and the second radiographic image G2 include primary radiation components and scattered radiation components of the radiations transmitted through the subject H.

The first and second radiation detectors 5 and 6 can repeatedly record and read out the radiographic images. So-called direct type radiation detectors that generate charges by directly receiving radiations may be used, or so-called indirect type radiation detectors that convert radiations into visible light and convert the visible light into charge signals may be used. Although it is desirable that a so-called thin film transistor (TFT) read-out method of reading out radiographic image signals by turning on and off a TFT switch or a so-called optical read-out method of reading out the radiographic image signals by irradiation of read-out light are used as a method of reading out the radiographic image signals, the present disclosure is not limited thereto, and other methods may be used.

A display unit 8 and an input unit 9 are connected to the console 2. The display unit 8 is a cathode ray tube (CRT), a liquid crystal display, or the like, and displays the radiographic images acquired by imaging and a soft part image and a bone part image to be described below or assists various inputs necessary for processing performed in the console 2.

The input unit 9 is a keyboard, a mouse, or an input device of a touch panel type, and receives an instruction to operate the imaging apparatus 1 from an operator. An instruction to input various kinds of information such as imaging conditions necessary to perform imaging and an instruction to correct information are also received. In the present embodiment, the units of the imaging apparatus 1 operate according to information input by the operator from the input unit 9.

An image processing program according to the present embodiment is installed on the console 2. The console 2 corresponds to the image processing apparatus according to the present embodiment. In the present embodiment, the console 2 may be a workstation or a personal computer directly operated by the operator, or may be a server computer connected to the workstation and the personal computer via a network. The image processing program is stored in a storage device of the server computer connected to the network or a network storage in a state of being accessible from the outside, and is downloaded and installed in the computer according to a request. Alternatively, the image processing program is distributed while being recorded in a recording medium such as a Digital Versatile Disc (DVD) or a compact disc read only memory (CD-ROM), and is installed on the computer from the recording medium.

Figure 2:
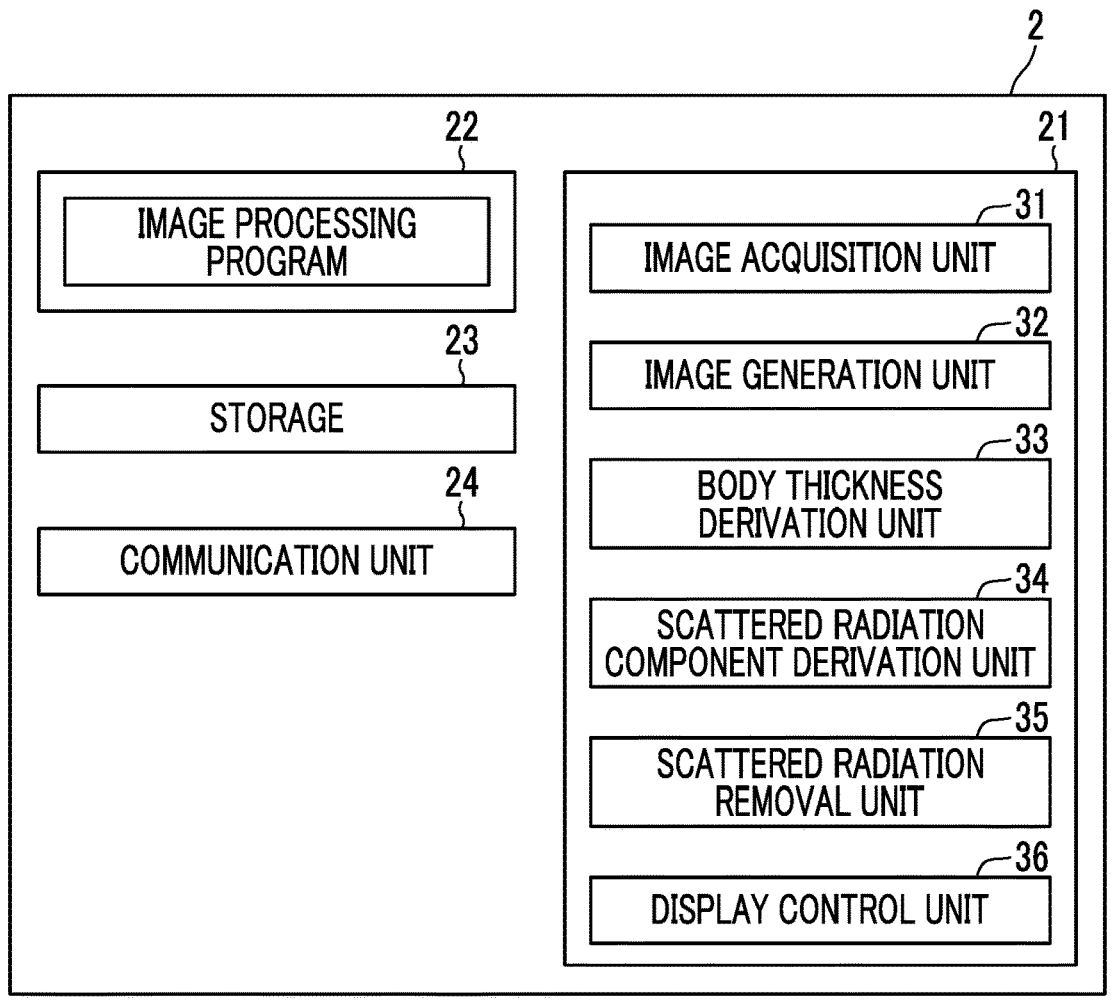
FIG. 2 is a diagram showing a schematic configuration of the image processing apparatus according to the first embodiment.

FIG. 2 is a diagram showing a schematic configuration of the image processing apparatus which is realized by installing the image processing program on the computer constituting the console 2. As shown in FIG. 2, the image processing apparatus includes a central processing unit (CPU) 21, a memory 22, a storage 23, and a communication unit 24 as a standard computer configuration.

The storage 23 is a storage device such as a hard disk drive or a solid state drive (SSD), and stores various kinds of information including programs for driving the units of the imaging apparatus 1 and the image processing program. The radiographic images acquired by imaging are also stored.

The communication unit 24 is a network interface that controls transmission of various kinds of information to an external apparatus via a network (not shown).

The memory 22 temporarily stores the program and the like stored in the storage 23 in order to cause the CPU 21 to execute various kinds of processing. The image processing program defines, as the processing to be executed by the CPU 21, image acquisition processing of acquiring the first and second radiographic images G1 and G2 having energy distributions different from each other by causing the imaging apparatus 1 to perform imaging, image generation processing of generating a contrast-reduced image in which contrast in a region other than the soft part in the first or second radiographic image G1 or G2 is reduced, body thickness derivation processing of deriving a body thickness of the subject H based on the contrast-reduced image, scattered radiation component derivation processing of deriving scattered radiation components of the radiations included in radiographic images based on the contrast-reduced image and the derived body thickness, scattered radiation removal processing of removing the scattered radiation components included in the radiographic images based on the derived scattered radiation components, and display control processing of displaying the first and second radiographic images G1 and G2 from which the scattered radiations are removed on the display unit 8.

The CPU 21 executes these processing according to the image processing program, and thus, the console 2 functions as an image acquisition unit 31, an image generation unit 32, a body thickness derivation unit 33, a scattered radiation component derivation unit 34, a scattered radiation removal unit 35, and a display control unit 36.

The image acquisition unit 31 irradiates the subject H with the radiations by driving the radiation source 3, detects the radiations transmitted through the subject H by the first and second radiation detectors 5 and 6, and acquires the first and second radiographic images G1 and G2. At this time, imaging conditions such as an imaging dose, an energy distribution, a tube voltage, and a source image distance (SID) are set. The imaging conditions may be set by inputs of the operator from the input unit 9. The set imaging conditions are stored in the storage 23. The first and second radiographic images G1 and G2 may be acquired by a program different from the image processing program and stored in the storage 23. In this case, the image acquisition unit 31 reads out the first and second radiographic images G1 and G2 stored in the storage 23 from the storage 23 in order to perform processing. In the present embodiment, it is assumed that a range from the chest to the abdomen of the subject H is captured and the first and second radiographic images G1 and G2 for the range from the chest to the abdomen are acquired.

Figure 3:
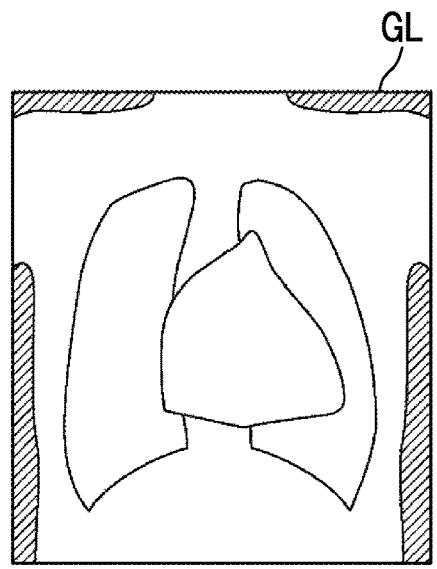
FIG. 3 is a diagram showing a contrast-reduced image.

The image generation unit 32 generates contrast-reduced images GL in which contrast in regions other than the soft parts in the first and second radiographic images G1 and G2 is reduced. In the first embodiment, the first and second radiographic images G1 and G2 are acquired by the imaging apparatus 1 capable of performing the energy subtraction by the one-shot method. Thus, the image generation unit 32 generates, as the contrast-reduced images GL, soft part images from which the soft parts in the subject H are extracted by performing subtraction processing of performing weighted subtraction on the first and second radiographic images G1 and G2 between the corresponding pixels as represented by the following Equation (1). α is a preset weighting factor. FIG. 3 is a diagram showing the contrast-reduced images GL which are the soft part images. As shown in FIG. 3, since the contrast-reduced images GL are the soft part images, the bone parts in the first and second radiographic images G1 and G2 are removed, and, as a result, the contrast of the bone parts is reduced.

$$GL(x,y)=\alpha \cdot G2(x,y)-G1(x,y) \tag{1}$$

The body thickness derivation unit 33 estimates the body thickness distribution of the subject H based on the imaging conditions in a case where the first and second radiographic images G1 and G2 are acquired and the contrast-reduced images GL. In the case of estimating the body thickness distribution, the body thickness derivation unit 33 generates low frequency contrast-reduced images GLs indicating low frequency components of the contrast-reduced images GL. Specifically, the low frequency contrast-reduced images GLs are generated by performing filtering processing using a low-pass filter on the contrast-reduced images GL. The low frequency contrast-reduced images GLs may be generated by using a known method such as wavelet transform and Fourier transform.

Figure 4:
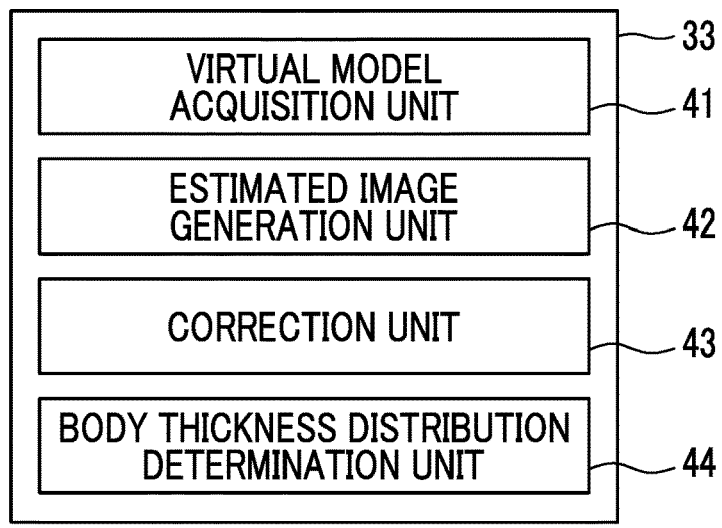
FIG. 4 is a schematic block diagram showing a configuration of a body thickness derivation unit.

In the present embodiment, the body thickness derivation unit 33 estimates the body thickness distribution of the subject H by using the method described in JP2015-043959, for example. FIG. 4 is a schematic block diagram showing a configuration of the body thickness derivation unit 33. As shown in FIG. 4, the body thickness derivation unit 33 includes a virtual model acquisition unit 41, an estimated image generation unit 42, a correction unit 43, and a body thickness distribution determination unit 44.

The virtual model acquisition unit 41 acquires a virtual model K of the subject H having an initial body thickness distribution T0(x, y). The virtual model K is generated in advance, and is stored in the storage 23.

The estimated image generation unit 42 obtains an image obtained by combining an estimated primary radiation image Igp obtained by estimating a primary radiation image obtained by imaging the virtual model K and an estimated scattered radiation image Igs obtained by estimating a scattered radiation image obtained by imaging the virtual model K by imaging the subject H, and generates, as an estimated image Im, an estimated image obtained by estimating the low frequency contrast-reduced image GLs obtained by the subtraction processing based on the virtual model K.

The correction unit 43 corrects the initial body thickness distribution T0 of the virtual model K based on the estimated image Im and the low frequency contrast-reduced image GLs such that a difference between the estimated image Im and the low frequency contrast-reduced image GLs becomes small.

The body thickness distribution determination unit 44 determines a corrected body thickness distribution Tn-1 (n is a natural number) as a body thickness distribution T(x, y) of the low frequency contrast-reduced images GLs.

The scattered radiation component derivation unit 34 calculates the primary radiation components and the scattered radiation components in the pixels of the radiographic images from the body thickness distribution T(x, y) of the subject H derived by the body thickness derivation unit 33 according to the following Equations (2) and (3), and derives, as the scattered radiation components, a scattered radiation content rate distribution S(x, y) from the calculated primary radiation components and scattered radiation components based on Equation (4). In the present embodiment, it is assumed that the scattered radiation components of the first radiographic image G1 acquired by the radiation detector 5 present on a side close to the subject H in the case of imaging are derived. The scattered radiation content rate distribution S(x, y) is a value between 0 and 1.

$$Ip(x,y)=Io(x,y)\times \exp(-\mu \times T(x,y)) \tag{2}$$

$$Is(x,y)=Io(x,y)*S\sigma(T(x,y)) \tag{3}$$

$$S(x,y)=Is(x,y)/(Is(x,y)+Ip(x,y)) \tag{4}$$

Here, (x, y) is coordinates of a pixel position of the first radiographic image G1, Ip(x, y) is a primary radiation component at the pixel position (x, y), Is(x, y) is a scattered radiation component at the pixel position (x, y), Io(x, y) is an incident dose on a surface of the subject H at the pixel position (x, y), μ is a linear attenuation coefficient of the subject H, and Sσ(T(x, y)) is a convolution kernel indicating scattering characteristics corresponding to the body thickness of the subject H at the pixel position (x, y). Equation (2) is an equation based on the known exponential attenuation law, and Equation (3) is an equation based on the method described in "J M Boon et al, An analytical model of the scattered radiation distribution in diagnostic radiolog, Med. Phys. 15(5), September/October 1988" (Cited Reference 1). The incident dose Io(x, y) on the surface of the subject H is canceled by division in the case of calculating S(x, y) even though any value is defined, and thus, any value may be used like an example in which a value is set to one.

Here, * in Equation (3) is an operator indicating a convolution operation. The nature of the kernel changes depending on a distribution of irradiation fields, a distribution of the compositions of the subject H, an irradiation dose in the case of performing the imaging, a tube voltage, an imaging distance, and the characteristics of the radiation detectors 5 and 6 in addition to the body thickness of the subject H. According to the method described in Cited Reference 1, the scattered radiation can be approximated by convolution of a point spread function (Sσ(T(x, y)) in Equation (3)) with respect to the primary radiation. Sσ(T(x, y)) can be experimentally obtained depending on irradiation field information, subject information, imaging conditions, and the like.

In the present embodiment, $S\sigma(T(x, y))$ may be calculated based on the irradiation field information, the subject information, and the imaging conditions in the case of performing the imaging. However, a table in which various kinds of irradiation field information, various kinds of subject information, and various imaging conditions are associated with $S\sigma(T(x, y))$ is stored in the storage 23, and $S\sigma(T(x, y))$ may be obtained based on the irradiation field information, the subject information, and the imaging conditions in the case of performing the imaging while referring to this table. $S\sigma(T(x, y))$ may be approximated by $T(x, y)$.

The scattered radiation removal unit 35 removes the scattered radiation components included in the first radiographic image G1 caused by the radiation scattered in the subject H by using the scattered radiation components derived by the scattered radiation component derivation unit 34. For example, any method described in JP2014-207958A and JP2015-043959A can be used as a method of removing the scattered radiation components. Hereinafter, the method described in JP2014-207958A will be described.

The scattered radiation removal unit 35 performs the scattered radiation removal processing by reducing frequency components of a frequency bandwidth that can be regarded as the scattered radiation in the first radiographic image G1 based on the scattered radiation component information derived by the scattered radiation component derivation unit 34. Thus, the scattered radiation removal unit 35 acquires the frequency component for each of the plurality of frequency bandwidths by performing frequency decomposition of the first radiographic image G1, performs processing of reducing a gain of at least one frequency component, combines the processed frequency components and other frequency components, and acquires a first radiographic image G1p obtained by the scattered radiation removal processing. As the frequency decomposition method, any known method such as a wavelet transform and a Fourier transform can be used in addition to a method of performing multi-resolution conversion on the radiographic image.

The scattered radiation removal unit 35 calculates a transform coefficient $R(x, y)$ for transforming the frequency components from a scattered radiation transmittance Ts, a primary radiation transmittance Tp which are virtual grid characteristics and the scattered radiation content rate distribution $S(x, y)$ by the following Equation (5). The scattered radiation transmittance Ts and the primary radiation transmittance Tp are acquired in advance, and are stored in the storage 23.

$$R(x,y)=S(x,y)\times Ts+(1-S(x,y))\times Tp \qquad (5)$$

Since the scattered radiation transmittance Ts, the primary radiation transmittance Tp, and the scattered radiation content rate distribution $S(x, y)$ are values between 0 and 1, the transform coefficient $R(x, y)$ is also a value between 0 and 1. The scattered radiation removal unit 35 calculates the transform coefficient $R(x, y)$ for each of the plurality of frequency bandwidths.

In the following description, it is assumed that a pixel value of the first radiographic image G1 is $I(x, y)$, a frequency component image obtained by frequency decomposition is $I(x, y, r)$, a frequency synthesis is $I(x, y)=\Sigma rI(x, y, r)$, a transform coefficient for each frequency bandwidth is $R(x, y, r)$, and a scattered radiation transmittance and a primary radiation transmittance for each frequency bandwidth are $Ts(r)$ and $Tp(r)$. r represents the hierarchy of the frequency bandwidth, and as r becomes larger, the frequency becomes lower. Accordingly, $I(x, y, r)$ becomes the frequency component image of a certain frequency bandwidth. The scattered radiation components derived by the scattered radiation component derivation unit 34 may be used as the scattered radiation content rate distribution $S(x, y)$, but may be derived by the scattered radiation component derivation unit 34 for each frequency bandwidth similarly to the scattered radiation transmittance Ts and the primary radiation transmittance Tp.

In the present embodiment, the transform coefficient $R(x, y, r)$ is calculated for each frequency component, the frequency component image $I(x, y, r)$ is multiplied by the transform coefficient $R(x, y, r)$ of the corresponding frequency bandwidth, the pixel value of the frequency component image $I(x, y, r)$ is converted, and a processed radiographic image $I'(x, y)$ is acquired by performing frequency synthesis on the frequency component image $I(x, y, r)$ multiplied by the transform coefficient $R(x, y, r)$ (that is, $I(x, y, r) \times R(x, y, r)$). Accordingly, the processing performed in the scattered radiation removal unit 35 is expressed by the following Equation (6). Since the transform coefficient $R(x, y, r)$ is a value between 0 and 1, the pixel value at the pixel position $(x, y)$ of the frequency component, that is, the gain is reduced by multiplying the frequency component $(x, y, r)$ by the transform coefficient $R(x, y, r)$ of the corresponding frequency bandwidth.

$$I'(x,y)=\Sigma r\{I(x,y,r)\times R(x,y,r)\}=\Sigma r\{I(x,y,r)\times (S(x,y)\times Ts(r)+(1-S(x,y))\times Tp(r))\} \qquad (6)$$

Here, in the present embodiment, it is assumed that the radiographic image is frequency-decomposed into six frequency bandwidths and the scattered radiation transmittance Ts and the primary radiation transmittance Tp are acquired for the six frequency bandwidths. In this case, the scattered radiation transmittance Ts and the primary radiation transmittance Tp are, for example, the values represented in the following Equation (7). In Equation (7), it is assumed that the value of the lower frequency bandwidth becomes lower toward the right.

$$Ts=\{0.7,0.7,0.7,0.7,0.3,0.2\}$$

$$Tp=\{0.7,0.7,0.7,0.7,0.7,0.7\} \qquad (7)$$

As shown in Expression (7), the scattered radiation transmittance Ts and the primary radiation transmittance Tp have the same value in the high frequency bandwidth (r=1 to 4), but the scattered radiation transmittance Ts has a lower value in the low frequency bandwidth (r=5 to 6). This is because the grid has a higher removal rate as the frequency bandwidth in which the frequency components of the scattered radiation are dominant becomes lower but has a low frequency dependency of the primary radiation on the removal rate.

The transform coefficient calculated based on Equations (5) and (7) has a smaller value in the region in which a content rate of the scattered radiations in the radiographic image becomes higher. Accordingly, in the processed radiographic image acquired by performing the processing represented in Equation (6) by using the transform coefficient calculated in this manner, the scattered radiation components are removed depending on the type of the grid expected to be used.

The scattered radiation removal unit 35 may remove the scattered radiation of the radiographic image as follows. First, in a case where it is assumed that frequency synthesis is represented by I(x, y)=Σrl(x, y, r) as described above, the scattered radiation removal unit 35 decomposes the frequency component image I(x, y, r) into the scattered radiation component Is(x, y, r) and the primary radiation component Ip(x, y, r) by using the scattered radiation content rate distribution S(x, y) by the following Equation (8).

$$Is(x,y,r)=S(x,y)\times I(x,y,r)$$

$$Ip(x,y,r)=(1-S(x,y))\times I(x,y,r) \qquad (8)$$

The scattered radiation removal unit 35 performs image conversion by applying the scattered radiation transmittance Ts(r) and the primary radiation transmittance Tp(r) which are the virtual grid characteristics to the scattered radiation component Is(x, y, r) and the primary radiation component Ip(x, y, r), and calculates the converted scattered radiation component Is'(x, y, r) and the primary radiation component Ip'(x, y, r) by the following Equation (9).

$$Is'(x,y,r)=Is(x,y,r)\times Ts(r)=S(x,y)\times I(x,y,r)\times Ts(r)$$

$$Ip'(x,y,r)=Ip(x,y,r)\times Tp(r)=(1-S(x,y))\times I(x,y,r)\times Tp(r) \qquad (9)$$

Then, the scattered radiation removal unit 35 performs the frequency synthesis of Is'(x, y, r) and the primary radiation component Ip'(x, y, r) according to the following Equation (10), and derives the processed radiographic image I'(x, y) from which the scattered radiation components in the first radiographic image G1 are removed, that is, the processed first radiographic image G1$p$.

$$I'(x,y)=\Sigma r\{Is'(x,y,r)+Ip'(x,y,r)\}=\Sigma r\{S(x,y)\times I(x,y,r)\times Ts(r)+(1-S(x,y))\times I(x,y,r)\times Tp(r)\}=\Sigma r\{I(x,y,r)\times (S(x,y)\times Ts(r)+(1-S(x,y))\times Tp(r))\} \qquad (10)$$

The display control unit 36 displays the processed first radiographic image G1$p$ from which the scattered radiation components are removed on the display unit 8.

Figure 5:
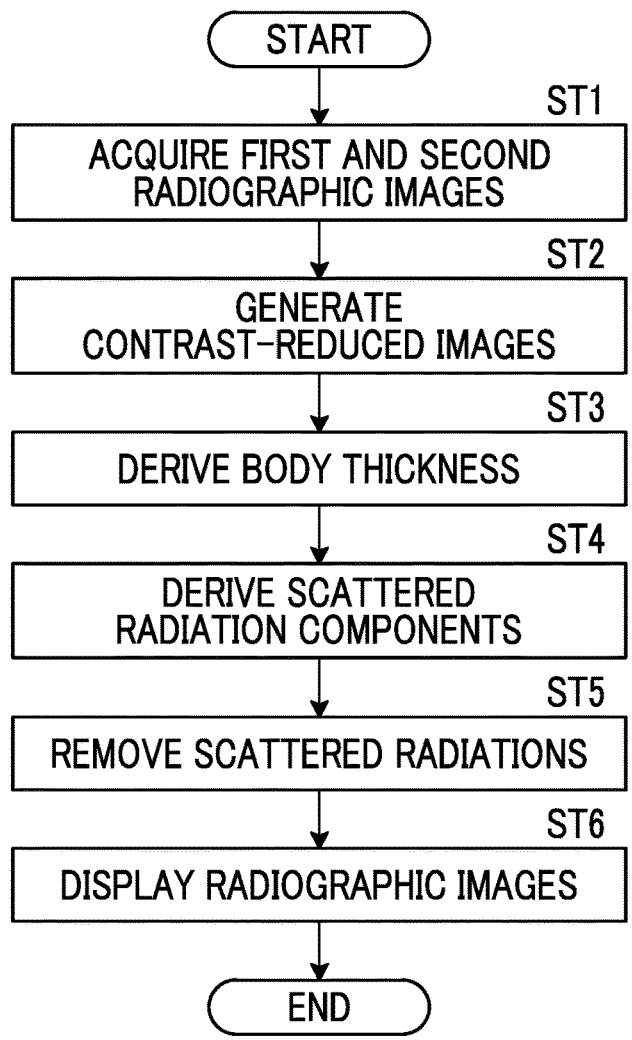
FIG. 5 is a flowchart showing processing performed in the first embodiment.

Next, processing performed in the first embodiment will be described. FIG. 5 is a flowchart showing the processing performed in the first embodiment. It is assumed that the first and second radiographic images G1 and G2 are acquired by imaging and are stored in the storage 23. In a case where an instruction to start the processing is input from the input unit 9, the image acquisition unit 31 acquires the first and second radiographic images G1 and G2 from the storage 23 (step ST1). Subsequently, the image generation unit 32 generates the contrast-reduced image GL in which the contrast of the first radiographic image G1 is reduced (step ST2). The body thickness derivation unit 33 derives the body thickness of the subject H based on the contrast-reduced image GL (step ST3).

Subsequently, the scattered radiation component derivation unit 34 derives the scattered radiation components of the radiation included in the first radiographic image G1 based on the contrast-reduced image GL and the derived body thickness (step ST4). The scattered radiation removal unit 35 removes the scattered radiation components included in the first radiographic image G1 based on the derived scattered radiation components (scattered radiation removal; step ST5). The display control unit 36 displays the processed first radiographic image G1$p$ from which the scattered radiation components are removed on the display unit 8 (radiographic image display; step ST6), and the processing is ended.

As described above, in the first embodiment, the contrast-reduced image GL in which the contrast other than the soft part in the first radiographic image G1 is reduced is generated, and the body thickness of the subject H is derived based on the contrast-reduced image GL. Here, in the contrast-reduced image GL, the contrast of the bone part of the subject H is reduced. Accordingly, according to the first embodiment, it is possible to reduce the influence of the bone part in the case of deriving the body thickness, and thus, it is possible to accurately derive the body thickness of the subject H. Since the body thickness of the subject H can be accurately derived, the scattered radiation components can also be accurately derived, and as a result, the scattered radiation components of the radiation included in the first radiographic image G1 can be accurately removed.

Figure 6:
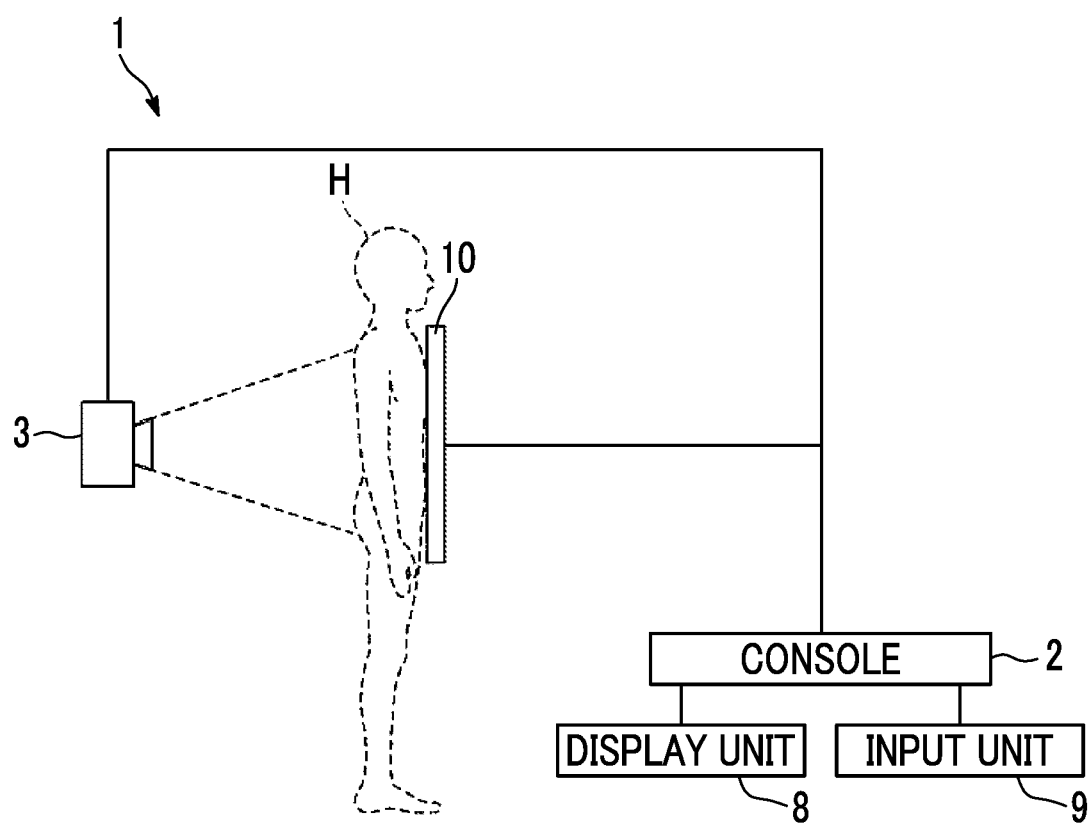
FIG. 6 is a schematic configuration diagram of a radiographic image imaging apparatus to which an image processing apparatus according to a second embodiment of the present disclosure is applied.

Next, a second embodiment of the present disclosure will be described. FIG. 6 is a schematic block diagram showing a configuration of a radiographic image imaging system to which an image processing apparatus according to a second embodiment of the present disclosure is applied. In FIG. 6, the same components as those in FIG. 1 are assigned by the same reference signs, and detailed description thereof will be omitted. An image processing apparatus according to the second embodiment has the same configuration as the image processing apparatus according to the first embodiment of the present disclosure shown in FIG. 2, and has a difference in only processing to be performed. Thus, the detailed description of the image processing apparatus is omitted herein. A radiographic image imaging system to which the image processing apparatus according to the second embodiment is applied is different from the first embodiment in that one radiographic image G3 is acquired by using one radiation detector 10 and the image generation unit 32 in the console 2 generates the contrast-reduced image GL by performing bone reduction processing on the radiographic image G3.

Here, processing of detecting a bone part region from the radiographic image G3 and reducing the contrast of the bone part region can be used as the bone reduction processing. A method of deriving a histogram of the radiographic image G3 and detecting a low-density (high-luminance) region in the histogram as a bone part region can be used to detect the bone part region. The bone part region may be detected by using a bone part detection model constructed by performing machine learning so as to detect the bone part region.

Processing of increasing the density of the bone part region and reducing a density difference from the soft part region can be used as the processing of reducing the contrast of the bone part region.

As stated above, the contrast of the bone part region in the radiographic image G3 can be reduced by performing the bone reduction processing on the radiographic image G3 to generate the contrast-reduced image GL. Accordingly, it is possible to reduce the influence of the bone part in the case of deriving the body thickness, and as a result, it is possible to accurately derive the body thickness of the subject H. Since the body thickness of the subject H can be accurately derived, the scattered radiation components can also be accurately derived, and as a result, the scattered radiation components of the radiation included in the radiographic image G3 can be accurately removed.

Next, a third embodiment of the present disclosure will be described. An image processing apparatus according to the third embodiment has the same configuration as the image processing apparatus according to the first embodiment of the present disclosure shown in FIG. 2, and has a difference in only processing to be performed. Thus, the detailed description of the apparatus is omitted herein. The image processing apparatus according to the third embodiment uses the radiographic image G3 acquired by the same radiographic image imaging system as that of the second embodiment. The third embodiment is different from the second embodiment in that the image generation unit 32 generates the contrast-reduced image GL by performing filtering processing using a low-pass filter on the bone part region of the radiographic image G3.

A method of deriving the histogram of the radiographic image G3 and detecting the low-density (high-luminance) region in the histogram as the bone part region as in the second embodiment can be used as the method of detecting the bone part region. The bone part region may be detected by using a bone part detection model constructed by performing machine learning so as to detect the bone part region.

The size of the low-pass filter may be determined depending on a size of the detected bone part region. For example, a low-pass filter having a size corresponding to a size of a rib may be used for a thin bone part such as a rib, and a low-pass filter having a size corresponding to a size of a vertebra may be used for a thick bone part such as a vertebra. Due to the filtering processing using the low-pass filter, the filtering processing is performed on a part of the soft part region adjacent to the bone part region. However, even though the filtering processing using the low-pass filter is performed on the soft part region, a large influence is not given in the case of deriving the body thickness.

As described above, the contrast-reduced image GL is generated by performing the filtering processing using the low-pass filter on the bone part region of the radiographic image G3, and thus, the contrast of the bone part region in the radiographic image G3 can be reduced. Accordingly, it is possible to reduce the influence of the bone part in the case of deriving the body thickness, and as a result, it is possible to accurately derive the body thickness of the subject H. Since the body thickness of the subject H can be accurately derived, the scattered radiation components can also be accurately derived, and as a result, the scattered radiation components of the radiation included in the radiographic image G3 can be accurately removed.

Although it has been described in the first embodiment that the scattered radiation components are derived by deriving the body thickness of the subject H based on the first radiographic image G1, the present disclosure is not limited thereto. The body thickness may be derived based on the second radiographic image G2 instead of the first radiographic image G1. In this case, the scattered radiation removal processing may be performed by deriving the scattered radiation components of the second radiographic image G2 by using the derived body thickness, and a processed second radiographic image G2p may be derived.

In addition to the first radiographic image G1, the body thickness may be derived for the second radiographic image G2, and the processed second radiographic image G2p from which the scattered radiation components are removed may be derived. In this case, the soft part image and the bone part image of the subject H may be derived by performing weighted subtraction processing between the corresponding pixels of the processed first radiographic image G1p and the processed second radiographic image G2p.

In the first embodiment, the contrast-reduced image GL may be generated by performing the bone reduction processing on the first and second radiographic images G1 and G2 as in the second embodiment. In the first embodiment, the contrast-reduced image GL may be generated by performing the filtering processing using the low-pass filter on the first and second radiographic images G1 and G2 as in the third embodiment.

Although it has been described in the first embodiment that the first and second radiographic images G1 and G2 are acquired by the one-shot method, the first and second radiographic images G1 and G2 may be acquired by a so-called two-shot method of performing imaging twice. In the case of the two-shot method, positions of the subject H included in the first radiographic image G1 and the second radiographic image G2 may shift due to a body movement of the subject H. Thus, it is preferable that the processing of the present embodiment is performed after the positions of the subject H in the first radiographic image G1 and the second radiographic image G2 are aligned. For example, the method described in JP2011-255060A can be used as the aligning processing. The method described in JP2011-255060A discloses that a plurality of first bandwidth images and a plurality of second bandwidth images indicating structures having different frequency bandwidths for each of the first and second radiographic images G1 and G2 are generated, the positional shift amount between the corresponding positions in the first bandwidth image and the second bandwidth image of the corresponding frequency bandwidth is acquired, and the positions of the first radiographic image G1 and the second radiographic image G2 are aligned based on the positional shift amount.

Although it has been described in the above-described embodiments that the processing is performed by using the radiographic images acquired in the system that images the radiographic images of the subject H by using the first and second radiation detectors 5 and 6 and the radiation detector 10, the present disclosure can be applied to a case where the first and second radiographic images G1 and G2 and the radiographic image G3 are acquired by using accumulative phosphor sheets as detection units. In this case, in the first embodiment, the first and second radiographic images G1 and G2 may be acquired by irradiating two overlapped accumulative phosphor sheets with the radiation transmitted through the subject H, accumulating and recording radiographic image information of the subject H in each accumulative phosphor sheet, and photoelectrically reading the radiographic image information from each accumulative phosphor sheet. The two-shot method may also be used in a case where the first and second radiographic images G1 and G2 are acquired by using the accumulative phosphor sheets.

The radiations in each of the above-described embodiments are not particularly limited, and a-rays or y-rays can be applied in addition to the X-rays.

In the above-described embodiments, the following various processors can be used as a hardware structure of processing units that execute various kinds of processing such as the image acquisition unit 31, the image generation unit 32, the body thickness derivation unit 33, the scattered radiation component derivation unit 34, the scattered radiation removal unit 35, and the display control unit 36 of the console 2 which is the image processing apparatus. As described above, in addition to the CPU which is a general-purpose processor that functions various processing units by executing software (programs), the various processors include a programmable logic device (PLD) which is a processor capable of changing a circuit configuration after a field programmable gate array (FPGA) is manufactured and a dedicated electrical circuit which is a processor having a circuit configuration specifically designed in order to execute specific processing such as an application specific integrated circuit (ASIC).

One processing unit may be constituted by one of these various processors, or may be constituted by a combination of two or more processors of the same type or different types (for example, a combination of a plurality of FPGAs or a combination of a CPU and an FPGA). The plurality of processing units may be constituted by one processor.

As an example in which the plurality of processing units is constituted by one processor, firstly, one processor is constituted by a combination of one or more CPUs and software as represented by computers such as clients and servers, and this processor functions as the plurality of processing units. Secondly, a processor that realizes the functions of the entire system including the plurality of processing units by one integrated circuit (IC) chip is used as represented by a system on chip (SoC). As described above, the various processing units are constituted by using one or more of the various processors as the hardware structure.

More specifically, an electric circuitry in which circuit elements such as semiconductor elements are combined can be used as the hardware structure of these various processors.

The image processing apparatus according to the present disclosure may further comprise a scattered radiation component derivation unit that derives scattered radiation components of a radiation included in the radiographic image based on the contrast-reduced image and the derived body thickness.

In this case, the image processing apparatus may further comprise a scattered radiation removal unit that removes the scattered radiation components included in the radiographic image based on the derived scattered radiation components.

In the image processing apparatus according to the present disclosure, the image generation unit may generate, as the contrast-reduced image, a soft part image obtained by extracting the soft part of the subject by acquiring two radiographic images based on radiations which are transmitted through the subject and have energy distributions different from each other and performing weighted subtraction using a predetermined weighting factor between corresponding pixels of the two radiographic images.

In the image processing apparatus according to the present disclosure, the two radiographic images may be acquired by two detection units overlapped with each other by simultaneously irradiating the two detection units with the radiations transmitted through the subject.

In the image processing apparatus according to the present disclosure, the image generation unit may generate the contrast-reduced image by performing bone reduction processing on the radiographic image.

In the image processing apparatus according to the present disclosure, the image generation unit may generate the contrast-reduced image by performing filtering processing using a low-pass filter on the bone part of the radiographic image.

What is claimed is:

1. An image processing apparatus comprising a processor that is configured to:
    extract a bone part region from a radiographic image indicating a subject including a soft part and a bone part, performing an image processing on the bone part region to increase an image density of the bone part region, and generate a contrast-reduced image in which contrast is reduced in a region other than the soft part that includes the processed bone part region having the increased image density; and
    derive a body thickness of the subject based on the contrast-reduced image.

2. The image processing apparatus according to claim 1, wherein the processor is further configured to derive scattered radiation components of a radiation included in the radiographic image based on the contrast-reduced image and the derived body thickness.

3. The image processing apparatus according to claim 2, wherein the processor is further configured to remove the scattered radiation components included in the radiographic image based on the derived scattered radiation components.

4. The image processing apparatus according to claim 1, wherein the processor generates, as the contrast-reduced image, a soft part image obtained by extracting the soft part of the subject by acquiring two radiographic images based on radiations which are transmitted through the subject and have energy distributions different from each other and performing weighted subtraction using a predetermined weighting factor between corresponding pixels of the two radiographic images.

5. The image processing apparatus according to claim 2, wherein the processor generates, as the contrast-reduced image, a soft part image obtained by extracting the soft part of the subject by acquiring two radiographic images based on radiations which are transmitted through the subject and have energy distributions different from each other and performing weighted subtraction using a predetermined weighting factor between corresponding pixels of the two radiographic images.

6. The image processing apparatus according to claim 3, wherein the processor generates, as the contrast-reduced image, a soft part image obtained by extracting the soft part of the subject by acquiring two radiographic images based on radiations which are transmitted through the subject and have energy distributions different from each other and performing weighted subtraction using a predetermined weighting factor between corresponding pixels of the two radiographic images.

7. The image processing apparatus according to claim 4, wherein the two radiographic images are acquired by two detection units overlapped with each other by simultaneously irradiating the two detection units with the radiations transmitted through the subject.

8. The image processing apparatus according to claim 5, wherein the two radiographic images are acquired by two detection units overlapped with each other by simultaneously irradiating the two detection units with the radiations transmitted through the subject.

9. The image processing apparatus according to claim 6, wherein the two radiographic images are acquired by two detection units overlapped with each other by simultaneously irradiating the two detection units with the radiations transmitted through the subject.

10. The image processing apparatus according to claim 1, wherein the processor generates the contrast-reduced image by performing bone reduction processing on the radiographic image.

11. The image processing apparatus according to claim 2, wherein the processor generates the contrast-reduced image by performing bone reduction processing on the radiographic image.

12. The image processing apparatus according to claim 3, wherein the processor generates the contrast-reduced image by performing bone reduction processing on the radiographic image.

13. The image processing apparatus according to claim 1, wherein the processor generates the contrast-reduced image by performing filtering processing using a low-pass filter on the bone part of the radiographic image.

14. The image processing apparatus according to claim 2, wherein the processor generates the contrast-reduced image by performing filtering processing using a low-pass filter on the bone part of the radiographic image.

15. The image processing apparatus according to claim 3, wherein the processor generates the contrast-reduced image by performing filtering processing using a low-pass filter on the bone part of the radiographic image.

16. An image processing method comprising:
extracting a bone part region from a radiographic image indicating a subject including a soft part and a bone part, performing an image processing on the bone part region to increase an image density of the bone part region, and generating a contrast-reduced image in which contrast is reduced in a region other than the soft part that includes the processed bone part region having the increased image density; and
deriving a body thickness of the subject based on the contrast-reduced image.

17. A non-transitory computer-readable storage medium storing an image processing program causing a computer to execute:
extracting a bone part region from a radiographic image indicating a subject including a soft part and a bone part, performing an image processing on the bone part region to increase an image density of the bone part region, and generating a contrast-reduced image in which contrast is reduced in a region other than the soft part that includes the processed bone part region having the increased image density; and
deriving a body thickness of the subject based on the contrast-reduced image.

18. The image processing apparatus according to claim 1, where the processor is further configured to:
derive a histogram of the radiographic image indicating the subject including the soft part and the bone part, detect a low-density region in the histogram as the bone part region, and generate the contrast-reduced image in which contrast is reduced in the bone part region.

19. The image processing method of claim 16, further comprising:
deriving a histogram of the radiographic image indicating the subject including the soft part and the bone part, detecting a low-density region in the histogram as the bone part region, and generating the contrast-reduced image in which contrast is reduced in the bone part region.

20. The non-transitory computer-readable storage medium of claim 17, wherein the image processing program further causes the computer to execute:
deriving a histogram of the radiographic image indicating the subject including the soft part and the bone part, detecting a low-density region in the histogram as the bone part region, and generating the contrast-reduced image in which contrast is reduced in the bone part region.

* * * * *